(12) United States Patent
Shimokawa et al.

(10) Patent No.: US 6,857,762 B2
(45) Date of Patent: Feb. 22, 2005

(54) RING ILLUMINATOR

(75) Inventors: Seiji Shimokawa, Kawasaki (JP);
Tatsuya Nagahama, Kawasaki (JP);
Kuniaki Obata, Yokohama (JP);
Hirotaka Matsubara, Kawasaki (JP)

(73) Assignee: Mitutoyo Corporation, Kawasaki (JP)

( * ) Notice: Subject to any disclaimer, the term of this patent is extended or adjusted under 35 U.S.C. 154(b) by 14 days.

(21) Appl. No.: 10/436,101

(22) Filed: May 13, 2003

(65) Prior Publication Data

US 2003/0231494 A1 Dec. 18, 2003

(30) Foreign Application Priority Data

May 17, 2002 (JP) ........................................ 2002-143462

(51) Int. Cl.[7] .............................................. F21V 5/00
(52) U.S. Cl. ..................... 362/245; 362/231; 362/241; 362/247; 362/800
(58) Field of Search ................................. 362/245, 231, 362/240, 241, 33, 268, 800, 575, 247, 301, 302, 304, 305, 346, 347, 297; 359/630, 385, 387, 389, 390, 634

(56) References Cited

U.S. PATENT DOCUMENTS

| | | | |
|---|---|---|---|
| 4,617,619 A | * 10/1986 | Gehly | ........................ 362/302 |
| 4,706,168 A | 11/1987 | Weisner | ........................ 362/18 |
| 5,038,258 A | 8/1991 | Koch et al. | .................. 362/237 |
| 5,580,163 A | 12/1996 | Johnson et al. | ............. 362/285 |
| 5,690,417 A | 11/1997 | Polidor et al. | ............... 362/244 |
| 6,053,621 A | 4/2000 | Yoneda | ...................... 362/245 |
| 6,334,699 B1 | 1/2002 | Gladnick | ..................... 362/268 |
| 6,614,596 B2 * | 9/2003 | Gladnick | .................... 359/630 |

* cited by examiner

*Primary Examiner*—Thomas M. Sember
*Assistant Examiner*—Bao Q Truong
(74) *Attorney, Agent, or Firm*—Oliff & Berridge, PLC

(57) ABSTRACT

A plurality of light emitting elements comprise a number of groups having light emitting colors different from each other. The light emitting element groups are arranged in ring shapes about an optical axis of an optical system in a plane or planes substantially orthogonal to the optical axis. A combining unit combines radiation light beams of different light emitting colors to generate illumination light having a given hue. The combining unit is provided downstream of the light emitting elements along a light emitting direction. A focusing unit focuses the illumination light in the direction toward the optical axis and is provided downstream of the combining unit. Accordingly, it is possible to direct illumination light having uniform and non-irregular hue, the hue corresponding to a surface color of an object to be measured, to the object to be measured.

20 Claims, 5 Drawing Sheets

RING ILLUMINATOR

BACKGROUND OF THE INVENTION

1. Field of Invention

This invention relates to a ring illuminator for an optical measuring apparatus.

2. Description of Related Art

Illumination of an object to be measured plays an extremely important role in obtaining a clear image of the object to be measured in an optical microscope. The illumination is important when attempting to optically focus on a portion of the object to be measured. The illumination is also important when capturing an image of the portion using an image processing type measuring apparatus such as a measuring microscope, a tool microscope, a projector or a three-dimensional image measuring apparatus. These devices are particularly useful in inspecting and measuring a shape and a size of the object to be measured based on the captured image of the object to be measured.

Known illumination methods used with such image processing type measuring apparatus or the like include a vertical downward radiation illumination method, which radiates illumination light to the object to be measured from substantially directly above the object to be measured. However, in many cases, the vertical downward radiation illumination method is used for measuring an object to be measured which has a relatively simple shape. Accordingly, when measuring an object to be measured having a complicated shape, such as, for example, a step-like object to be measured having a large number of edge portions, shadows of the edge portions often cannot be clearly detected.

To solve such a drawback, a ring illuminator has been proposed that can clearly detect shadows of edge portions. The ring illuminator operates by radiating illumination light to the object to be measured from a direction that is inclined at a given angle with respect to an optical axis of an optical system of the image processing type measuring apparatus.

A known optical fiber light source is typically used as the light source for the ring illuminator. In general, this optical fiber light source guides illumination light radiated from a halogen lamp or the like through optical fibers. However, the halogen lamp or the like also has disadvantages, including a large power consumption, a short lifetime and/or a slow response rate when controlling the lighting intensity and upon being turned on and off.

Such ring illuminators typically adjust luminance and an illumination angle of illumination light radiated to the object to be measured. One method for accomplishing this forms fiber light sources into groups, and, for each group, independently controls the lighting intensity and activation of that group. To accomplish this independent control, separate lamps are provided for the groups of light sources and the intensity and activation of each lamp must be separately controlled. Alternately, shutter devices or the like, which allow light to be controllably transmitted or interrupted, are located either in the midst of, or at end portions of, the optical fibers. However, the shutter devices for each group must likewise be separately controlled. However, this necessitates a large number of lamps or shutters and the structure becomes complicated. Hence, the illuminator becomes overly large and the manufacturing cost increases.

On the other hand, recently, light emitting elements, such as, for example, light emitting diodes (LED), have been attracting attention in view of the characteristics of these sources, such as, for example, rapid responsivity, a long lifetime and the like. Such light emitting elements have begun to be used as light sources in various technical fields, along with the enhancement of luminance of the light emitting elements. For example, a ring illuminator has been proposed that uses light emitting diodes as light sources to solve the above-outlined drawbacks of the above-mentioned halogen lamps or the like to enable control of the lighting intensity and activation of the light sources.

For example, a ring illuminator is proposed in U.S. Pat. No. 5,690,417 (the 417 patent). In the ring illuminator of the 417 patent, a large number of light emitting diodes are provided as light sources. These light emitting diodes are concentrically arranged in a plurality of circular arrays, such as the five arrays used in an embodiment of the 417 patent. Respective light emitting diodes are mounted such that their light emitting directions are set towards the object to be measured. Further, in the 417 patent, a method is disclosed in which, as a modification of a focusing method, the light emitting directions of respective light emitting diodes are arranged parallel to an optical axis, where Fresnel lenses are arranged downstream of the light emitting directions to focus light on the object to be measured.

Further, in the ring illuminator disclosed in the 417 patent, the light emitting diodes are formed into groups of respective circular arrays and circumferential sectors. The lighting intensity and activation of each group and sector can be separately controlled. Accordingly, it is possible to controllably adjust the lighting intensity and activation of the light emitting diodes arranged in the plurality of arrays. Hence, the distribution of light to the object to be measured can be properly adjusted.

However, in the ring illuminator of the 417 patent, the light beams radiating from respective light emitting diodes that face the object to be measured have intrinsic divergence angles. Thus, those light beams spread out before reaching the object to be measured. Hence, the illumination efficiency is not sufficiently enhanced. Therefore, it is necessary to install an extremely large number of light emitting diodes to ensure the necessary illumination is obtained.

Further, the 417 patent discloses mounting Fresnel lenses in front of light emitting diodes to enhance the illumination efficiency by focusing the illumination light on the object to be measured. However, this does not correct the above-mentioned intrinsic divergence angles of the light emitting diodes. Hence, it is difficult to achieve a remarkable enhancement of illumination efficiency even with this technique.

Further, such Fresnel lenses have intrinsic focal lengths. However, a distance (i.e., the operable distance) between the object to be measured and the ring illuminator changes as the object to be measured changes. Consequently, the focal length and the operable distance of the Fresnel lens are displaced from each other. This results in the illumination light spreading, which lowers the illumination efficiency. Further, to maintain the illumination efficiency, the operable distance cannot be changed. Hence, it is difficult to obtain an optimum illumination light for every object to be measured.

Further, another known ring illuminator controls an illumination angle with respect to an object to be measured and an illumination direction of the illumination light to clearly detect conditions of edges and a surface of the object to be measured. In this known ring illuminator, plural types of rings are prepared. In each type of ring, light emitting diodes are mounted in a ring shape corresponding to specific illumination angles. The light emitting diodes of these rings are simultaneously or separately turned on to control the illumination angle. Further, the light emitting diodes are formed into groups in the circumferential direction for every ring. The lighting intensity and activation of the light emitting diodes of these circumferential groups are controllable so that the distribution of light to the object to be measured can be properly adjusted.

However, in these known ring illuminators, in the same manner as the above-mentioned 417 patent, due to divergence angles of light beams that radiate from respective ones of the light emitting diodes, the illumination efficiency is not sufficiently enhanced. Hence, it is necessary to mount a large number of light emitting diodes to ensure the necessary illumination. Further, it is necessary to mount plural types of rings, where different rings provide different illumination angles. Consequently, the structure of the illuminator becomes complicated.

On the other hand, the types of objects to be inspected or measured by an image processing type measuring apparatus or the like are extremely varied. The objects to be measured include electronic parts, such as printed circuit boards (PCB) or the like, mechanical parts, semiconductor parts, printed matter and the like. Further, the objects to be measured also have various surface colors. In the image processing type measuring apparatus or the like, a shape or the like of the object to be measured in an image captured using a CCD (Charge Coupling Device) or the like is recognized by detecting position of edges or the like within the image. By illuminating the colored object to be measured using illumination light having a hue (i.e., a tone of color) that corresponds to a surface color of the object to be measured, the contrast within the captured image can be improved. The contrast between elements within an obtained image is emphasized so that the detection accuracy of edges in the image can be further enhanced.

In the ring illuminators discussed above that are capable of controlling the hue of such illumination light, a plurality of several different types, such as, for example, three different types of light emitting diodes, have respective different light emitting colors, such as, for example, red (R), green (G) and blue (B). In such ring illuminators, lighting intensity or activation is controlled for the light emitting diodes of each color to control the hue of the illumination light.

However, in the ring illuminators discussed previously, since the illumination efficiency is low, it is necessary to arrange a large number of light emitting diodes. As a result, the ring illuminator becomes overly large and the manufacturing cost increases. Further, as described above, it is possible to control the hue of the illumination light by arranging several types of light emitting diodes having different light emitting colors. In such ring illuminators, the light beams emitted toward the object to be measured from the light emitting diodes of respective light emitting colors are combined on the object to be measured. However, the distances and the angles of the different color light beams of the respective light emitting diodes on the object to be measured are not the same. Hence, the hue of the generated illumination light is not uniform across the object. Consequently, an image of sufficiently high accuracy cannot be obtained.

SUMMARY OF THE INVENTION

This invention provides a ring illuminator having a reduced size.

This invention separately provides a ring illuminator that can sufficiently enhance the accuracy of the image detection.

This invention separately provides a ring illuminator that enhances the illumination efficiency of the object to be measured.

In various exemplary embodiments, a ring illuminator according to this invention includes a light source having a plurality of light emitting elements. The light emitting elements are arranged around an optical axis of an optical system. The light emitting elements are formed of at least two groups of light emitting elements having light emitting colors that are different from each other. In various exemplary embodiments, for each group of light emitting elements of the same type, those light emitting elements are arranged in a ring shape around the optical axis in a single plane, which, in various exemplary embodiments, is substantially orthogonal to the optical axis. A combining unit is located downstream of the light emitting directions of the light emitting elements. The combining unit combines radiation light beams, radiated from the light emitting elements, having light emitting colors different from each other. The combining unit outputs combined illumination light having a given hue. Further, a focusing unit is located downstream of an advancing direction of the combined illumination light. The focusing unit focuses the combined illumination light at a given position along the optical axis.

In various exemplary embodiments, the ring shape of the light emitting elements around the optical axis includes a circular annular arrangement, a triangular annular arrangement, a quadratic annular arrangement, a polygonal annular arrangement including a pentagonal annular arrangement or any other appropriate closed curve arrangement about the optical axis. Further, an elliptical annular arrangement or an oblong annular arrangement around the optical axis are also included in the ring shape.

In various exemplary embodiments, radiation light beams radiating from differently-colored light emitting elements are combined by the combining unit arranged downstream of the radiation light beams to form the combined illumination light of a given hue. The combined illumination light is focused at given position by the focusing unit. In this manner, the combined illumination light output by the combining unit can be used to illuminate an object to be measured. Hence, it is possible to illuminate the object to be measured with illumination light having a uniform hue that is appropriate for a surface color of the object to be measured. Accordingly, the contrast within an image obtained by an optical system is emphasized so that the accuracy of detection of edges or the like of the object to be measured can be sufficiently enhanced. Further, the illumination efficiency can be enhanced by focusing the illumination light to a given position using the focusing unit. Thus, the mounting number of light emitting elements can be reduced so that the size of the ring illuminator can be reduced.

In various exemplary embodiments, each group of light emitting element of a particular color is arranged in a ring shape and is spaced apart from the other groups of light emitting elements of other colors at a given distance along the optical axis from the combining unit. The light emitting element groups may have their light emitting directions arranged in a direction extending away from the optical axis.

In various exemplary embodiments, by arranging the light source such that the light emitting direction of the light emitting elements is along a direction substantially orthogonal to the optical axis of the optical system and away from the optical axis, the size of the ring illuminator including the combining unit and the focusing unit in the direction parallel to the optical axis can be reduced. Accordingly, when mounting the ring illuminator to an optical system, the freedom in positioning the ring illuminator along the optical axis is increased, the focusing range and the focusing position can be set with high accuracy, and/or the detection accuracy of the image of the object to be measured can be enhanced.

In various exemplary embodiments, the differently colored light emitting element groups may be arranged in the closed curve along circles which differ in distance from the optical axis on substantially the same planes that are substantially orthogonal to the optical axis. In these exemplary embodiments, the light emitting direction is substantially parallel to the optical axis.

In various exemplary embodiments, by arranging the light source such that the light emitting direction of the light emitting elements is substantially parallel to the optical axis of the optical system, the size of the ring illuminator according to this invention in the radial direction about the optical axis can be reduced. Accordingly, in measuring an object after mounting the ring illuminator to the optical system, the ring illuminator does not obstruct the measuring operation and the measuring operation can be rapidly performed.

In various exemplary embodiments, the plurality of light emitting elements may use three different types of light emitting diodes having, respectively, red (R), green (G) and blue (B) light emitting colors.

In various exemplary embodiments, by using typical light emitting diodes, it is possible to provide a light source which exhibits high responsivity, a long lifetime and the like. At the same time, by uniformly combining respective red (R), green (G) and blue (B) colors, which are the three primary (additive) colors of light, a white light which is the basic color of the illumination light can be produced. At the same time, by properly changing the combined amounts of the respective red (R), green (G) and blue (B) color light beams, the combined illumination light having any desired hue can be produced. Accordingly, the illumination light can be radiated that has various desired hues corresponding to the various surface colors of objects to be measured, so that the accuracy of detection of edges or the like of the objects to be measured can be further sufficiently enhanced.

In various exemplary embodiments, the combining unit includes dichroic mirrors formed in a planar shape.

Dichroic mirrors allow light to pass through the mirror or reflect light from the mirror based on a wavelength of light. Accordingly, by selectively reflecting or transmitting the light beams radiated from the light emitting elements and having light emitting colors which differ from each other, it is possible to combine the light beams having different light emitting colors to produce the combined illumination light having a given hue. Further, when dichroic mirrors having a simple planar shape are used, it is possible to inexpensively manufacture the combining unit. Further, compared to using dichroic mirrors having a curved surface, the loci of the reflected light and the transmitted light can be easily determined. Accordingly, the dichroic mirrors can be easily arranged and mounted. At the same time, the combining operation of the illumination light can be accurately performed.

In various exemplary embodiments, the dichroic mirrors may have characteristics that reflect light having a wavelength shorter than a given wavelength and that allow light having a wavelength longer than the given wavelength to pass through the dichroic mirrors. Alternatively, in various other exemplary embodiments, the dichroic mirrors may have characteristics that allow light having a wavelength shorter than a given wavelength to pass through the dichroic mirrors and that reflect light having a wavelength longer than the given wavelength.

In various exemplary embodiments, the dichroic mirrors switch from reflective to transmissive or from transmissive to reflective corresponding to the wavelength of light only once and at a given wavelength. Hence, compared to dichroic mirrors that switch between reflective and transmissive modes two or more times at a plurality of different wavelengths, the number of layers of a mirror surface vapor-deposition film is small. As a result, the film forming processing is facilitated and the reflection and transmission efficiency of the dichroic mirrors can be enhanced.

In various exemplary embodiments, an output direction of the combined illumination light generated by the combining unit may be on a plane that is substantially orthogonal to the optical axis and that extends away from the optical axis. In various exemplary embodiments, the focusing unit includes a reflection mirror that focuses the combined illumination light in the optical axis direction. In various exemplary embodiments, the reflection mirror includes a reflection surface having respective given curvatures with respect to two cross-sectional directions parallel to and orthogonal to the optical axis.

In various exemplary embodiments, the combined illumination light is reflected along the optical axis direction by the reflection mirror. In various exemplary embodiments, the reflection mirror is positioned further from the optical axis than the light source and the combining unit. Hence, an illumination angle of the combined illumination light directed onto the object to be measured is increased. Accordingly, when the object to be measured has a stereoscopic shape or the like, it is possible to clearly detect shadows of edge portions of the object to be measured. Further, a curvature of the reflection surface of the reflection mirror focuses the combined illumination light onto a given position of the object to be measured. Hence, it is possible to radiate the combined illumination light onto the position to be measured of the object to be measured in a concentrated manner. As a result, the illumination efficiency can be enhanced.

In various exemplary embodiments, an output direction of the combined illumination light generated by the combining unit is substantially parallel to the optical axis. In various exemplary embodiments, the focusing unit includes a first reflection mirror that reflects the combined illumination light away from the optical axis and a second reflection mirror that focuses the combined illumination light reflected from the first reflection mirror. In various exemplary embodiments, at least one of the first reflection mirror and the second reflection mirror includes a reflection surface having respective given curvatures with respect to two cross-sectional directions parallel to and orthogonal to the optical axis.

In various exemplary embodiments, by directing the radiation direction of the radiation light from the light source and the combined illumination light output from the combining unit parallel to the optical axis, and by providing a reflection mirror at a position close to the object to be measured, the size of the ring illuminator in the radial direction about the optical axis can be reduced. In various exemplary embodiments, the reflection surface of either the first reflection mirror or the second reflection mirror is curved to focus the combined illumination light to a given position on the object to be measured. Alternatively, in various exemplary embodiments, the reflection surfaces of both the first and second reflection mirrors are curved to focus the combined illumination light to a given position on the object to be measured. Hence, it is possible to radiate the combined illumination light onto a position to be measured of an object to be measured in a concentrated manner. As a result, the illumination efficiency can be enhanced.

In various exemplary embodiments, the light source and the combining unit may be fixed to an illuminator body. In various exemplary embodiments, the focusing unit is mounted such that the focusing unit is relatively movable substantially parallel to the optical axis with respect to an illuminator body. In various exemplary embodiments, the ring illuminator includes an adjusting unit that adjusts a position of the object to be measured onto which the illumination light is focused by relatively moving of the illuminator body and the focusing unit.

In various exemplary embodiments, by allowing relative movement between the illuminator body and the focusing unit along the optical axis, the combined illumination light can be reflected onto the reflection surface of the reflection mirror having a curved surface at different positions. Because the reflection surface is curved, at each different position, the reflection surface has a different inclination angle relative to the reflected combined illumination light. Hence, the reflection angle of the combined illumination light is different for each different position of the curved reflection surface. Accordingly, it is possible to adjust the illumination angle with respect to an object to be measured. Hence, combined illumination light having a desired illumination angle corresponding to the size, the shape and the surface condition of the object to be measured can be obtained. As a result, the accuracy of the detection of edges or the like of the object to be measured can be further enhanced.

In various exemplary embodiments, an output direction of the combined illumination light output by the combining unit is substantially parallel to the optical axis. In various exemplary embodiments, the focusing unit includes a substantially torus-shaped lens having a hole at a center portion of the torus-shaped lens.

In various exemplary embodiments, using the torus-shaped lens, which is a general-purpose optical element, the ring illuminator can be manufactured at a low cost. At the same time, by using a lens having high transmissivity and high accuracy, the transmission loss of the combined illumination light can be suppressed to a small amount. Likewise it is possible to accurately focus the combined illumination light over an illumination range to further enhance the illumination efficiency. Further, in various exemplary embodiments, the objective lens or the like which constitute the optical system can penetrate the ring illuminator through the hole formed in the center portion of the torus-shaped lens. Accordingly, the light reflected from the object to be measured can reach the objective lens or the like without being interrupted. Hence, the measurement of the object to be measured can be surely performed.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of the systems and methods of this invention will be described in detail, with reference to the following figures, wherein.

DETAILED DESCRIPTION OF EXEMPLARY EMBODIMENTS

Various exemplary embodiments of a ring illuminator according to this invention are explained in detail in conjunction with various drawings figures. In the following explanation, identical or substantially similar constitutional elements are given the same numerals and their explanation is omitted or simplified.

Figure 1:
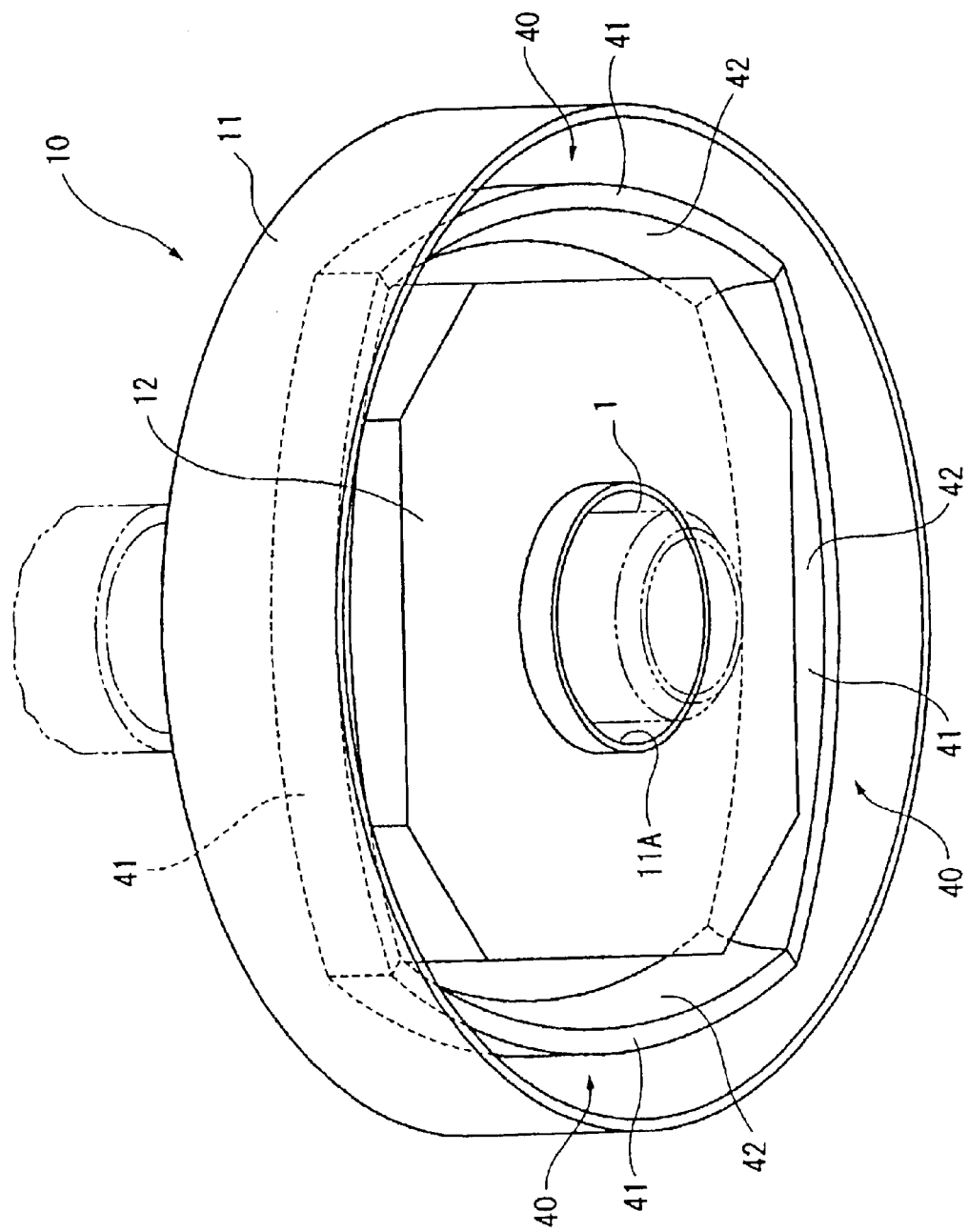
FIG. 1 is a perspective view showing a first exemplary embodiment ring illuminator according to this invention.
Figure 2:
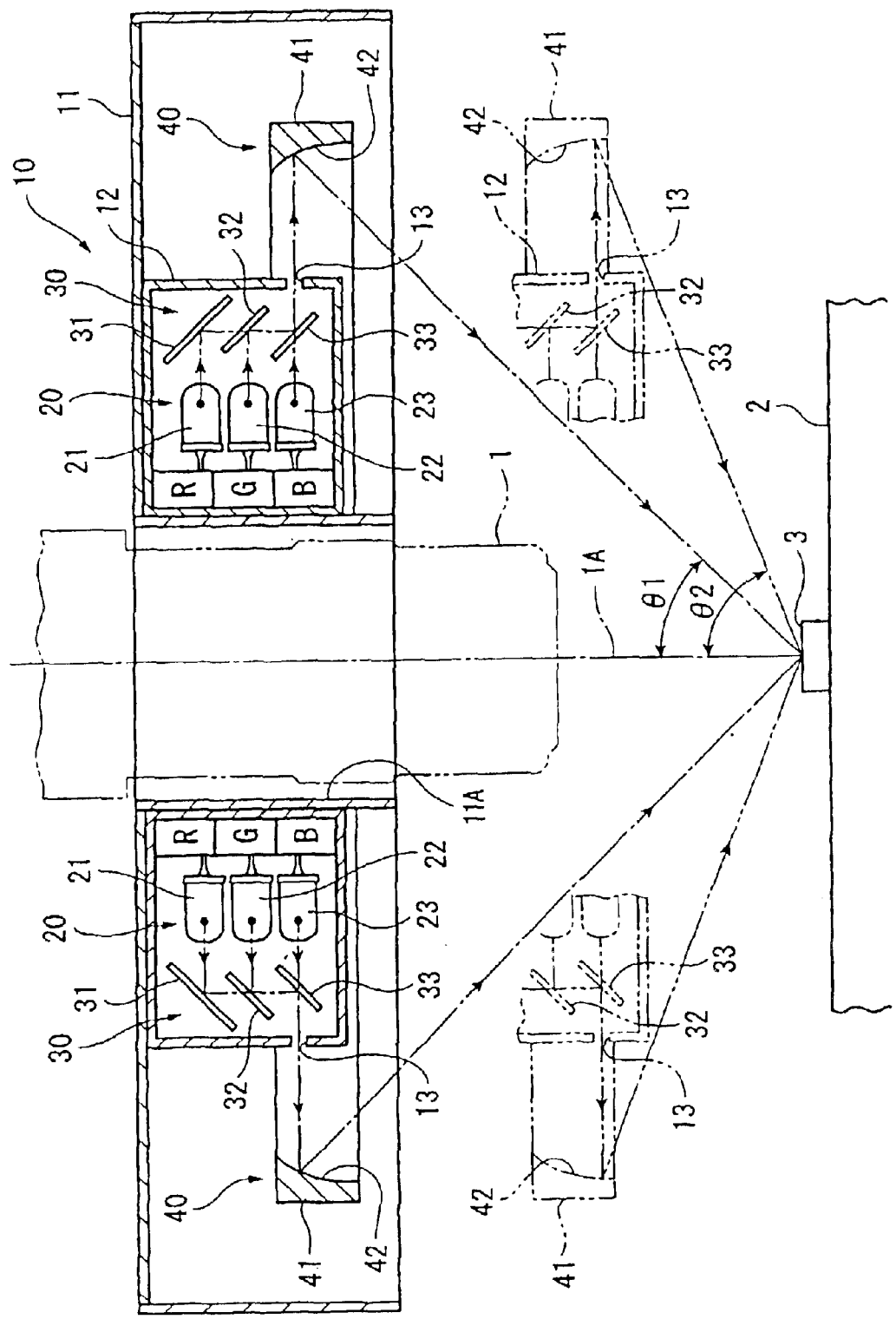
FIG. 2 is a cross-sectional view of the ring illuminator shown in FIG. 1.
Figure 3:
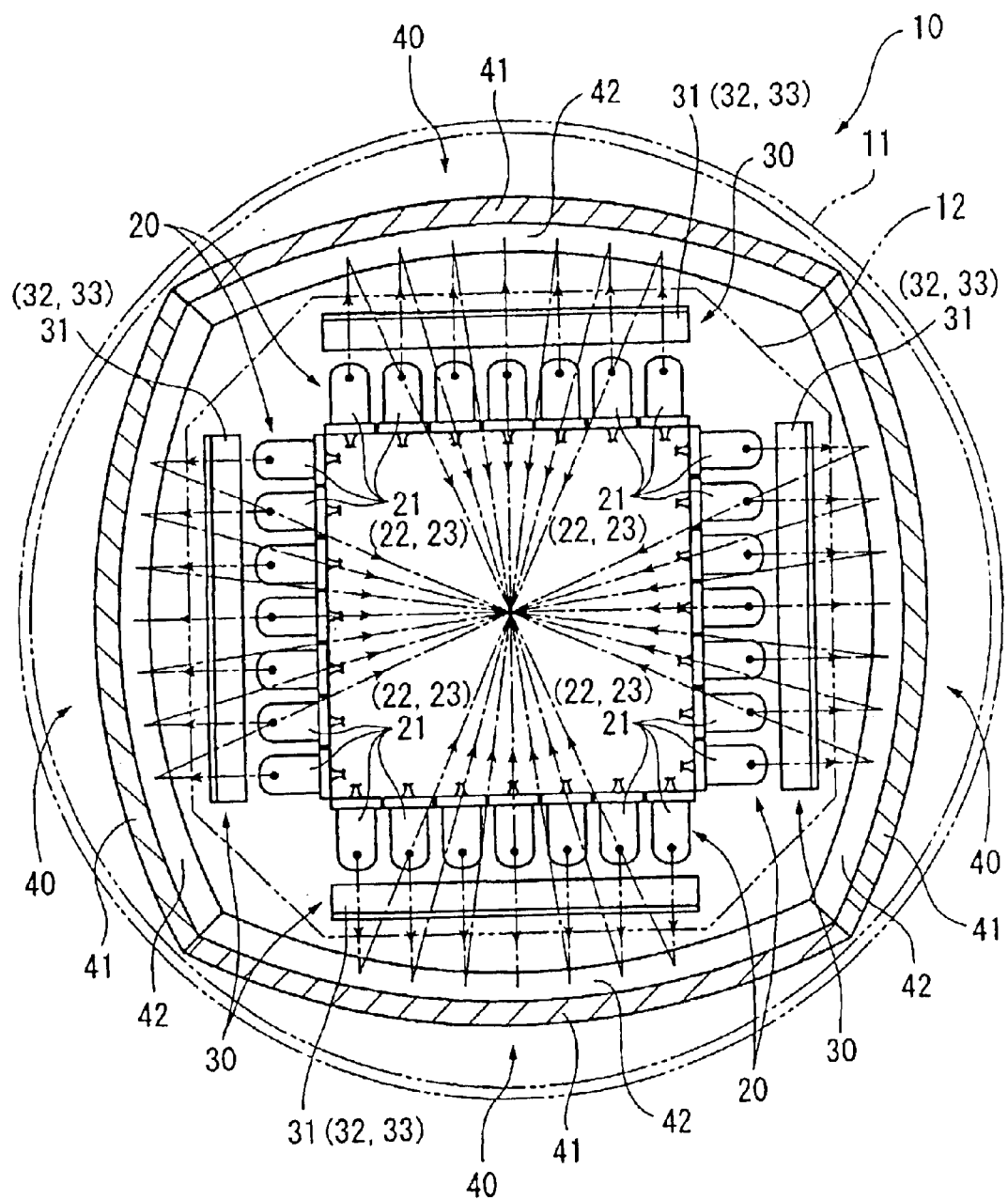
FIG. 3 is a bottom view of the ring illuminator shown in FIG. 1.

A first exemplary embodiment of ring illuminator 10 according to this invention is shown in FIG. 1 to FIG. 3. Second and third exemplary embodiments, of ring illuminators 50 and 60 according to this invention are respectively shown in FIG. 4 and FIG. 5.

FIG. 1 is an overall perspective view of the ring illuminator 10, FIG. 2 is a cross-sectional view of the ring illuminator 10 and FIG. 3 is a bottom view of the ring illuminator 10 with a part in cross section. In FIG. 1 to FIG. 3, the ring illuminator 10 illuminates an object to be measured 3 (i.e., a work piece), which is placed on a measuring base console 2 of an image measuring device (not shown in the drawing). The illuminator 10 is mounted on an objective lens 1, which constitutes at least a portion of a magnification optical system of the image measuring device or the like. In the image measuring device, the measuring base console 2 is subjected to a drive control in two orthogonal axes directions within a horizontal plane, that is, in a left-and-right direction as well as in a front-and-back direction in FIG. 2. A driving device (not shown in the drawing) is used to move the measuring base console 2 along the two orthogonal directions. Further, by controllably driving the objective lens 1 in the vertical direction, that is, in the up-and-down direction in FIG. 2, it is possible to adjust a position and a measuring distance of the objective lens 1 appropriately to obtain an image of a portion to be measured of the object to be measured 3.

The ring illuminator 10 includes a casing 11 which surrounds the objective lens 1 and which constitutes an illuminator body. The casing 11 is formed in a ring shape around an optical axis 1A of the objective lens 1. The ring illuminator 10 also includes a light source box 12 that is mounted inside the casing 11 at a side of the casing 11 close to the objective lens 1. A plurality of light emitting diodes 20 and a group of mirrors 30 are provided inside the light source box 12. The plurality of light emitting diodes 20 constitute a light source of the ring illuminator 10. The group of mirrors 30 constitute a combining unit of the ring illuminator 10. A reflection mirror 40 is arranged around the light source box 12 and constitutes a focusing unit of the ring illuminator 10. As shown in FIG. 2, the position of the objective lens 1 in the vertical direction is determined such that the objective lens 1 is spaced apart from the object to be measured 3 by a given measuring distance. Here, the illumination light is radiated on the object to be measured 3 at an illumination angle θ1 corresponding to a distance (referred to herein as the operable distance) between the ring illuminator 10 mounted on the objective lens 1 and the object to be measured 3.

In various exemplary embodiments, the casing 11 is formed by processing a metal sheet or the like and is formed in a ring shape which opens downwardly, as shown in FIG. 2. As also shown in FIG. 2, a lens through hole 11A vertically penetrates a central portion of the casing 11. The lens through hole 11A of the casing 11 has an inner diameter size which allows the objective lens 1 to pass through the lens through hole 11A with tolerance. Further, a mounting portion (not shown in the drawing), which mounts the ring illuminator 10 to the objective lens 1 in a state that the objective lens 1 passes through the casing 11, is formed on the casing 11. For example, three screws which are supported on the casing 11 such that the screws can be moved toward or retracted from the objective lens 1 can be used as such a mounting portion.

In various exemplary embodiments, the light source box 12 is formed by processing a metal sheet or the like in the same manner as the casing 11. In various exemplary embodiments, the light source box 12 is formed of a box-like member having a substantially octagonal plan shape in which corner portions of a substantially rectangular shape are chamfered. In various exemplary embodiments, in various ones of four faces of the light source box 12 at sides remote from the objective lens 1, slits 13 are formed along a plane substantially orthogonal to the optical axis 1A.

Light emitting diodes 20 have at least three types of light emitting colors, such as, for example, red, green and blue, are provided inside of the light source box 12. As shown in FIG. 2, the light emitting diodes 20 are arranged such that along the optical axis 1A, red (R) light emitting diodes 21, green (G) light emitting diodes 22 and blue (B) light emitting diodes 23 are sequentially arranged along the vertical direction. In various exemplary embodiments, the groups of the light emitting diodes 21, 22 and 23 are spaced apart from each other at a given interval and, as shown in FIGS. 1 and 3, are arranged in a substantially rectangular planar shape about the optical axis 1A on planes which are respectively substantially orthogonal to the optical axis 1A. As shown in FIG. 3, in various exemplary embodiments, each of the groups of light emitting diodes 21, 22 and 23 includes seven light emitting diodes along each side of the substantially rectangular planar shape. Each set of light emitting diodes along a side are arranged such that they are substantially orthogonal to adjacent sets. The light emitting directions of the light emitting diodes of each set are directed away from the optical axis 1A.

Each of the light emitting diodes 20 includes a focusing lens mounted on distal end, in the light emitting direction, of that light emitting diode 20, such that divergence angle of the emitted illumination light beam of that light emitting diode 20 assume a given angle (for example, 20°). The light emitting diodes 20 are connected to a control circuit and a power source (not shown in the drawing).

As shown in FIGS. 2 and 3, mirror groups 30 are positioned downstream, along the light emitting directions, from the light emitting diodes 20. In particular, one mirror group 30 is provided for each of the sets of light emitting diodes arranged along a given side of the substantially rectangular shape. Each mirror group 30 includes at least three mirrors 31, 32 and 33. The respective mirrors 31, 32 and 33 are each formed in a substantially rectangular planar shape. In each mirror group 30, the longitudinal directions of the mirrors 31, 32 and 33 are arranged substantially parallel to the rows of the corresponding sets of the light emitting diodes 21, 22 and 23. A longitudinal length of the mirrors 31, 32 and 33 is substantially equal to length of the respective side of the substantially planar rectangular shape into which the light emitting diodes 20 are arranged. In various exemplary embodiments, the mirrors 31, 32 and 33 are inclined at substantially 45° with respect to the optical axis 1A in the cross-sectional direction along the optical axis 1A.

As shown in FIG. 2, the mirrors 31 are reflection mirrors and are arranged to reflect the light radiated from the red light emitting diodes 21 toward the object to be measured 3 along the optical axis 1A.

The mirrors 32 and 33 are dichroic mirrors and either reflect light beams having wavelengths shorter than a given wavelength and allow light beams having wavelengths longer than the given wavelength to pass through the mirror, or allow light beams having wavelengths shorter than a given wavelength to pass through the mirror and reflect light beams having wavelengths longer than the given wavelength. That is, the mirrors 32 and 33 are dichroic mirrors which have a single transition either from reflective to transmissive, or from transmissive to reflective, at the given wavelength.

The mirror 32 is arranged such that the mirror 32 allows the red light reflected by the mirror 31 to pass through the mirror 32, while it reflects the green radiation light radiated from the green light emitting diode 22, which has a wavelength that is shorter than the wavelength of the red light, in the direction toward the object to be measured 3 along the optical axis 1A.

The mirror 33 is arranged such that the mirror 33 reflects the red light which passes through the mirror 32 and the green light which is reflected by the mirror 32 and allows the blue radiation light, which is radiated from the blue light emitting diode 23 and has a wavelength shorter than the wavelengths of the red and green light beams, to pass through the mirror 33. Thus, the mirrors 31, 32 and 33 act to combine the red, green and blue emitted light beams into a single combined light beam. It should be appreciated that, if the order of the red, green and blue light emitting diodes 21, 22 and 21 were altered, the types of the dichroic mirrors and the location of the reflective mirror would change accordingly. Likewise, if the location of the slit 13 were altered relative to the order of the red, green and blue light emitting diodes 21, 22 and 23, the types of the dichroic mirrors and the location of the reflective mirror would change accordingly.

The illumination light which is formed by combining the red and green lights reflected by the mirror 33 and the blue light which passes through the mirror 33 travels from the mirror 33 along an advancing direction (that is, downstream of the direction away from the optical axis 1A on a plane which is substantially orthogonal to the optical axis 1A). A reflection mirror 40 is arranged downstream along the advancing direction from the mirror 33. The reflection mirror 40 is provided between respective planar rectangular sides of the light source box 12 and the casing 11. The relative position of the reflection mirror 40 with respect to the light source box 12 is movable along the optical axis 1A by a driving device (not shown in the drawing) that is mounted inside the casing 11.

In various exemplary embodiments, the reflection mirror 40 is constituted by a metal reflection mirror body 41. A side surface of the reflection mirror body 41 at a side which faces the optical axis 1A is provided with a mirror finish, thus forming a reflection surface 42 that reflects the combined illumination light. As shown in FIG. 2, the reflection surface 42 has a first convex curvature in the direction away from the optical axis 1A with respect to the cross-sectional direction along the optical axis 1A, such that the combined illumination light is reflected toward the object to be measured 3. A shown in FIGS. 1 and 3, with respect to a plane that is substantially orthogonal to the optical axis 1A, the reflection surface 42 has a second a convex curvature. This second convex curvature has a radius that is substantially twice the distance from the optical axis 1A to the reflection mirror 40 in the direction away from the optical axis 1A. Accordingly, the combined illumination light, which advances away from the optical axis 1A in the direction substantially parallel to the light emitting direction of the light emitting diodes 20 arranged in the substantially rectangular shape, is reflected toward the optical axis 1A.

Initially, the position of the objective lens 1 with respect to the set measuring distance is adjusted corresponding to the size, the shape and the measuring range of the object to be measured 3. As indicated above, the ring illuminator 10 is mounted on the objective lens 1 and thus moves with the objective lens 1.

To adjust the hue of the illumination light in response to the hue of the object to be measured 3, appropriate ones of the red, green and blue light emitting diodes 21, 22 and 23 are selectively activated to obtain a combined illumination light have the appropriate color. In particular, the lighting or emission intensity and the activation of the light emitting diodes 21, 22 and 23 is controlled. That is, when all of the red, green and blue light emitting diodes 21, 22, 23 are turned on, the combined illumination light output by the mirror groups 30 is a white light. In contrast, when only one of the red, green or blue light emitting diodes 21, 22 or 23 are turned on, a combined illumination light of such a color is obtained. Further, when any two of the light emitting diodes 21, 22 and 23 red, green and blue are turned on, the combined illumination light having the two selected colors is obtained. Further, by partially turning on or off any one or two of the light emitting diodes 21, 22 and 23, it is possible to output a combined illumination light having an intermediate color.

Further, to provide a proper illumination angle depending on the shape of a surface to be measured of the object to be measured 3, the illumination angle of the combined light output from the ring illuminator 10 can be adjusted. For example, as shown in FIG. 2, when edges of irregularities of the object to be measured 3 having many irregularities on a surface thereof is to be detected, the illumination angle can be set to a large illumination angle θ2. In various exemplary embodiments, to be able to adjust the illumination angle, the reflection mirror 40 is mounted in the ring illuminator 10 so that the reflection mirror 40 is movable relative to the casing 11 and the light source box 12. In this case, as indicated by a chain double-dashed line in FIG. 2, the reflection mirror 40 moved in the direction away from the object to be measured 3 along the optical axis 1A. At the same time, the mounting position of the ring illuminator 10 on the objective lens 1 is set to a position close to the object to be measured 3. Because of such an arrangement, the combined illumination light output by the mirror group 30 of the light source box 12 passes through the slits 13 of the light source box 12 and is reflected on a position of the reflection surface 42 of the reflection mirror 40 which is close to the object to be measured 3. That is, the combined light is incident on a position of the reflection surface 42 having a curvature where the inclination angle with respect to the optical axis 1A is small. Accordingly, the reflected illumination light is directed onto the object to be measured 3 at the large illumination angle θ2 with respect to the optical axis 1A.

Alternatively, in various other exemplary embodiments, the light source box 12 can be moved relative to the casing 11 and the reflection mirror 40 to control the location of the point of incidence of the combined illumination light on the reflection surface 42. Alternatively, in still other exemplary embodiments, both the light source box 12 and the reflection mirror 40 are movable relative to the casing 11.

In various exemplary embodiments of the first exemplary embodiment of the ring illuminator 10 shown in FIGS. 1–3, the light beams that radiate from the red, green and blue light emitting diodes 21, 22 and 23 are combined to form a combined illumination light of a given hue by the mirror group 30 including the dichroic mirrors 32 and 33. The dichroic mirrors 32 and 33 are arranged in front of two of the light emitting diodes 21, 22 and 23. The combined illumination light is directed to the object to be measured 3. Hence, it is possible to illuminate the surface of the object to be measured 3 with illumination light having a hue corresponding to a surface color of the object to be measured 3. In response, the contrast within the image of the object to be measured 3 obtained through the objective lens 1 is emphasized. Hence, it is possible to sufficiently enhance the accuracy of detection of edges or the like of the object be measured 3 in the obtained image.

In various exemplary embodiments of the first exemplary embodiment of the ring illuminator 10 shown in FIGS. 1–3, by combining the radiated light beams output from the red, green and blue light emitting diodes 21, 22 and 23 using the mirror groups 30, the combined illumination light that is preliminarily combined into the given hue by the mirror group 30 is directed to the object to be measured 3. Accordingly, compared to situations in which the light beams of respective colors are combined at the surface of the object to be measured 3, it is possible to radiate the combined illumination light having a uniform hue free from irregularities, so that the detection accuracy can be further enhanced.

In various exemplary embodiments of the first exemplary embodiment of the ring illuminator 10 shown in FIGS. 1–3, by concentrating the illumination light on the object to be measured 3 by the reflection mirror 40, the illumination efficiency is enhanced. Consequently, the number of light emitting diodes 20 required in the ring illuminator 10 can be reduced. As a result, the size of the ring illuminator 10 can be reduced.

In various exemplary embodiments of the first exemplary embodiment of the ring illuminator 10 shown in FIGS. 1–3, compared to the related art, the number of light emitting diodes 20 required in the ring illuminator 10 can be reduced. Hence, the adverse influence of heat generated from the light emitting diodes 20 on the image measuring device or the like can be reduced. At the same time, the power consumption and the power cost of the ring illuminator can be reduced.

In various exemplary embodiments of the first exemplary embodiment of the ring illuminator 10 shown in FIGS. 1–3, by using the light emitting diodes 20 as the light source, it is possible to provide a light source having the more-rapid responsivity and the longer lifetime which are features of light emitting diodes. Further, by providing with the provision of the light emitting diodes 21, 22 and 23 of different colors, the white illumination light can be generated. At the same time, by properly changing the ratio of red, green and blue light on the combined illumination light, it is possible to generate illumination light beams having various hues. Accordingly, it is possible directed illumination light of an optimum hue or desired hue to the object to be measured 3 corresponding to the object to be measured 3 having various surface colors.

In various exemplary embodiments of the first exemplary embodiment of the ring illuminator 10 shown in FIGS. 1–3, by using the dichroic mirrors 32 and 33 as part of the mirror group 30 that forms the combining unit, it is possible to output illumination light of the given hue. Further, by forming the dichroic mirrors 32 and 33 in a substantially rectangular planar simple shape, it is possible to form the mirror group 30 in an inexpensive manner. Still further, compared to a case in which dichroic mirrors having curved surfaces are used, the loci of the reflected and transmitted light beams can be easily determined. Hence, it is possible to arrange and mount the dichroic mirrors 32 and 33 easily. At the same time, it is possible to accurately combine the illumination light from the various groups of the red, green and blue light emitting diodes 21, 22 and 23.

In various exemplary embodiments of the first exemplary embodiment of the ring illuminator 10 shown in FIGS. 1–3, the mirrors 32 and 33 are dichroic mirrors in which there is only a single transition from reflective to transmissive or from transmissive to reflective, corresponding to a given wavelength of the light. Accordingly, compared to dichroic mirrors that transition from reflective to transmissive or from transmissive to reflective at a plurality of different wavelengths of the light, the number of layers of mirror surface vapor deposited films of the dichroic mirrors 32 and 33 can be reduced. Hence, the film forming processing can be facilitated and, at the same time, the reflection transmission efficiencies of the dichroic mirrors 32 and 33 can be enhanced.

In various exemplary embodiments of the first exemplary embodiment of the ring illuminator 10 shown in FIGS. 1–3, by forming the ring illuminator 10 such that the light emitting direction of the light emitting diodes 20 is substantially orthogonal to the optical axis 1A and extends away from the optical axis 1A, and by positioning the mirror group 30 and the reflection mirror 40 downstream of the light emitting diodes 20 along the light emitting direction, the size of the ring illuminator 10 along the optical axis 1A can be reduced. Hence, the degree of freedom of the mounting position of the ring illuminator 10 to the objective lens 1 along the optical axis 1A is enhanced. As a result, the operable distance and the illumination angle can be accurately set and the detection accuracy for the image of the object to be measured 3 can be enhanced.

In various exemplary embodiments of the first exemplary embodiment of the ring illuminator 10 shown in FIGS. 1–3, the reflection mirror 40 is provided at a position further from the optical axis 1A than the light source box 12. The illumination light is reflected towards the optical axis 1A from the reflection mirror 40. Hence, the illumination angle of the illumination light radiated to the object to be measured 3 can be controlled. Consequently, shadows of edge portions of the object to be measured 3 having a stereoscopic shape can be clearly detected. Since the curvature used to focus the illumination light to the given position on the object to be measured is provided to the reflection surface 42 of the reflection mirror 40, it is possible to direct the illumination light to the position to be measured of the object to be measured 3 in a concentrated manner so that the illumination efficiency is enhanced.

In various exemplary embodiments of the first exemplary embodiment of the ring illuminator 10 shown in FIGS. 1–3, the convex curvature is provided to the reflection surface 42 of the reflection mirror 40 in the direction away from the optical axis 1A with respect to two directions. In various exemplary embodiments of the first exemplary embodiment of the ring illuminator 10 shown in FIGS. 1–3, these two directions include the cross-sectional direction along the optical axis 1A and a planar direction that is substantially orthogonal to the optical axis 1A. Accordingly, it is possible to direct the illumination light to the position to be measured of the object to be measured 3 in a concentrated manner so that the illumination efficiency can be enhanced.

In various exemplary embodiments of the first exemplary embodiment of the ring illuminator 10 shown in FIGS. 1–3, due to the first convex curvature, by allowing the reflection mirror 40 to move along the optical axis 1A with respect to the casing 11 and the light source box 12, the illumination light is reflected from the reflection surface 42 of the reflection mirror 40 at a position having a different inclination angle and the reflection angle can be changed. As a result, the illumination angle of the combined illumination light on the object to be measured 3 can be adjusted. Accordingly, it is possible to obtain illumination light having a desired illumination angle, which can be selected based on the size, the shape and/or the surface condition of the object to be measured 3. Thus, it is possible to achieve further enhancement in the accuracy for detecting the edges or the like of the object to be measured 3 in the obtained image.

Figure 4:
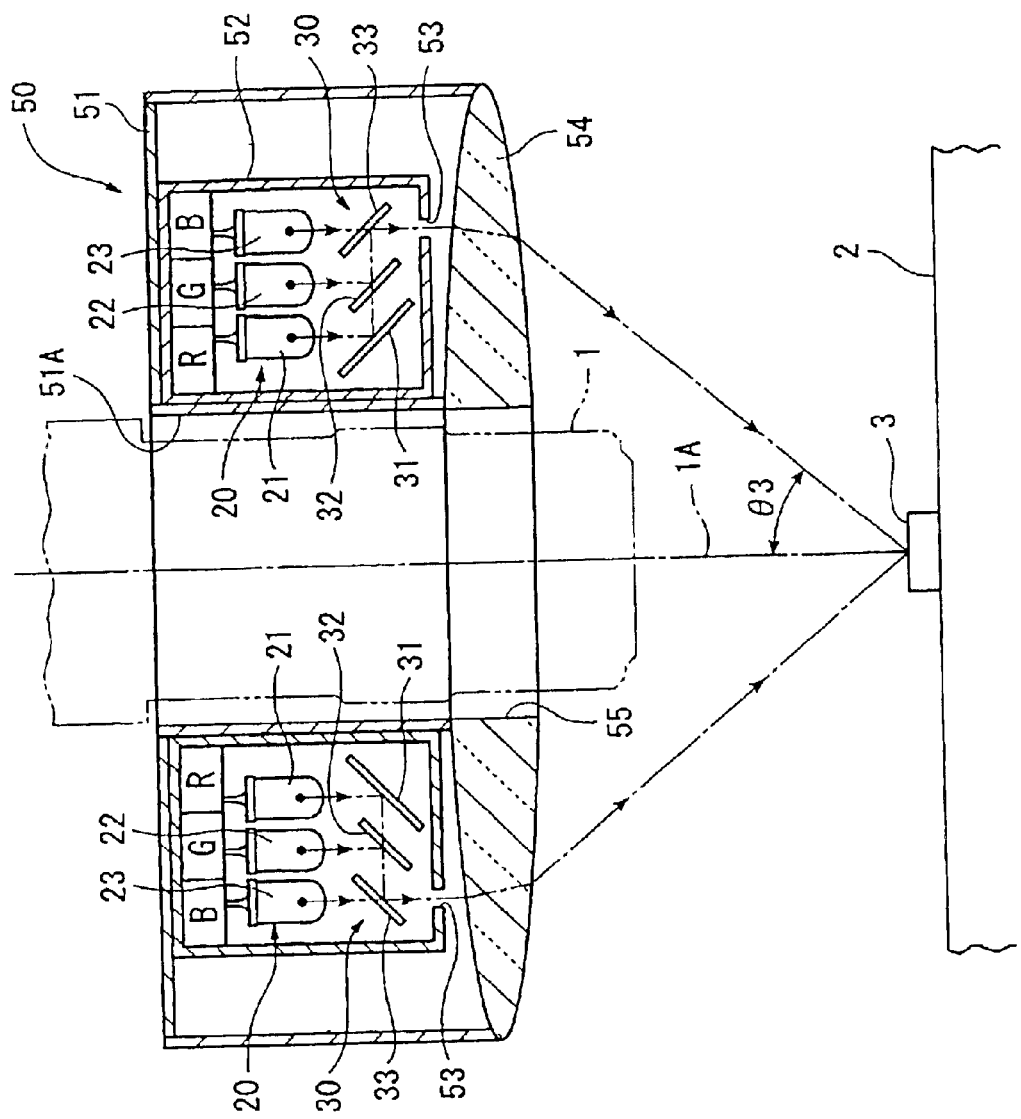
FIG. 4 is a cross-sectional view of a second exemplary embodiment of a ring illuminator according to this invention.

FIG. 4 is a cross-sectional view of a second exemplary embodiment of a ring illuminator 50 according to this invention. The ring illuminator 50 differs from the ring illuminator 10 in the orientation of the light emitting diodes 20 relative to the optical axis and in that a lens 54 is used in place of the reflection mirror 40 as the focusing unit. In other respects, the ring illuminator 50 is substantially similar to the ring illuminator 10.

As shown in FIG. 4, the red, green and blue light emitting diodes 21, 22 and 23 are arranged in a ring shape on one or more planes that are substantially orthogonal to the optical axis 1A. The light emitting diodes 21, 22 and 23 are each arranged in a substantially rectangular shape surrounding the optical axis 1A. The substantially rectangular shape differ in distance from the optical axis 1A for the different sets of light emitting diodes 21, 22 and 23, which are, in various exemplary embodiments, spaced apart from each other at a given interval. In the exemplary embodiment shown in FIG. 4, from the side closest to the optical axis 1A, the light emitting diodes 21 of red color (R), the light emitting diodes 22 of green color (G) and the light emitting diodes 23 of blue color (B) are sequentially arranged. The light emitting directions of the light emitting diodes 20 are arranged substantially parallel to the optical axis 1A such that the light emitting directions are toward the object to be measured 3.

Mirror groups 30, which are generally similar to the mirror groups 30 of the above-mentioned first embodiment of the ring illuminator 10, are arranged downstream of the light emitting directions of the light emitting diodes 20. Because of these mirror groups 30, the light beams radiated from the red, green and blue light emitting diodes 21, 22 and 23 are reflected by a mirror of the mirror group 30, or are allowed to pass through that mirror of the mirror group 30, in a direction away from the optical axis 1A. The mirrors groups 30 of the ring illuminator 50 combined the light emitted by the light emitting diodes 20 in a manner similar to that of the mirror groups 30 of the ring illuminator 10 to form the combined illumination light of a given hue. The combined illumination light is output from the mirror groups 30 substantially parallel to the optical axis 1A and advances toward the object to be measured 3.

As shown in FIG. 4, the ring illuminator 50 includes a light source box 52, which houses the light emitting diodes 20 and the mirror group 30. The light source box 52 is provided with slits 53 that allow the illumination light to pass out of the light source box 52. The slits 53 are provided in a bottom wall of the light source box 52 that faces the object to be measured 3. In various exemplary embodiments, the slits 53 are formed in the bottom wall at a location that is spaced away from the objective lens 1.

As shown in FIG. 4, the ring illuminator 50 includes a casing 51 on which the light source box 52 is mounted. The casing 51 is formed in a downwardly opened ring shape, as shown in FIG. 4. A lens through hole 51A vertically penetrates a center portion of the casing 51.

As shown in FIG. 4, the ring illuminator 50 includes a lens 54 mounted on the opening side of the casing 51. The lens 54 forms at least a portion of a focus unit that focuses the combined illumination light onto the object to be measured 3. In various exemplary embodiments, the lens 54 is made of transparent glass and has a substantially torus shape. In various exemplary embodiments, the lens 54 has a center that is substantially aligned with the optical axis 1A. The lens 54 has a central hole substantially aligned with the optical axis 1A. A thickness of the lens 54 gradually decreases from the central hole 55 towards an outer periphery of the lens 54. The lens 54 deflects the combined illumination light which passes through the slits 53 of the light source box 52 and focuses the combined illumination light onto the object to be measured 3 at an illumination angle θ3 corresponding to a focal length of the lens 54.

In various exemplary embodiments of the second exemplary embodiment of the ring illuminator 40 shown in FIG. 4, the light beams that radiate from the red, green and blue light emitting diodes 21, 22 and 23 are combined to form a combined illumination light of a given hue by the mirror groups 30, including the dichroic mirrors 32 and 33. The dichroic mirrors 32 and 33 are arranged in front of two of the light emitting diodes 21, 22 and 23. The combined illumination light is directed to the object to be measured 3. Hence, it is possible to illuminate the surface of the object to be measured 3 with illumination light having a hue corresponding to a surface color of the object to be measured 3. In response, the contrast within the image of the object to be measured 3 obtained through the objective lens 1 is emphasized. Hence, it is possible to sufficiently enhance the accuracy of detection of edges or the like of the object be measured 3 in the obtained image.

In various exemplary embodiments of the second exemplary embodiment of the ring illuminator 40 shown in FIG. 4, by combining the radiated light beams output from the red, green and blue light emitting diodes 21, 22 and 23 using the mirror groups 30, the combined illumination light that is preliminarily combined into the given hue by the mirror group 30 is directed to the object to be measured 3. Accordingly, compared to situations in which the light beams of respective colors are combined at the surface of the object to be measured 3, it is possible to radiate the combined illumination light having a uniform hue free from irregularities, so that the detection accuracy can be further enhanced.

In various exemplary embodiments of the second exemplary embodiment of the ring illuminator 40 shown in FIG. 4, by concentrating the illumination light on the object to be measured 3 by the reflection mirror 40, the illumination efficiency is enhanced. Consequently, the number of light emitting diodes 20 required in the ring illuminator 10 can be reduced. As a result, the size of the ring illuminator 10 can be reduced.

In various exemplary embodiments of the second exemplary embodiment of the ring illuminator 40 shown in FIG. 4, compared to the related art, the number of light emitting diodes 20 required in the ring illuminator 10 can be reduced. Hence, the adverse influence of heat generated from the light emitting diodes 20 on the image measuring device or the like can be reduced. At the same time, the power consumption and the power cost of the ring illuminator can be reduced.

In various exemplary embodiments of the second exemplary embodiment of the ring illuminator 40 shown in FIG. 4, by using the light emitting diodes 20 as the light source, it is possible to provide a light source having the more-rapid responsivity and the longer lifetime which are features of light emitting diodes. Further, by providing with the provision of the light emitting diodes 21, 22 and 23 of different colors, the white illumination light can be generated. At the same time, by properly changing the ratio of red, green and blue light on the combined illumination light, it is possible to generate illumination light beams having various hues. Accordingly, it is possible directed illumination light of an optimum hue or desired hue to the object to be measured 3 corresponding to the object to be measured 3 having various surface colors.

In various exemplary embodiments of the second exemplary embodiment of the ring illuminator 40 shown in FIG. 4, by using the dichroic mirrors 32 and 33 as part of the mirror group 30 that forms the combining unit, it is possible to output illumination light of the given hue. Further, by forming the dichroic mirrors 32 and 33 in a substantially rectangular planar simple shape, it is possible to form the mirror group 30 in an inexpensive manner. Still further, compared to a case in which dichroic mirrors having curved surfaces are used, the loci of the reflected and transmitted light beams can be easily determined. Hence, it is possible to arrange and mount the dichroic mirrors 32 and 33 easily. At the same time, it is possible to accurately combine the illumination light from the various groups of the red, green and blue light emitting diodes 21, 22 and 23.

In various exemplary embodiments of the second exemplary embodiment of the ring illuminator 40 shown in FIG. 4, the mirrors 32 and 33 are dichroic mirrors in which there is only a single transition from reflective to transmissive or from transmissive to reflective, corresponding to a given wavelength of the light. Accordingly, compared to dichroic mirrors that transition from reflective to transmissive or from transmissive to reflective at a plurality of different wavelengths of the light, the number of layers of mirror surface vapor deposited films of the dichroic mirrors 32 and 33 can be reduced. Hence, the film forming processing can be facilitated and, at the same time, the reflection transmission efficiencies of the dichroic mirrors 32 and 33 can be enhanced.

In various exemplary embodiments of the second exemplary embodiment of the ring illuminator 40 shown in FIG. 4, by forming the ring illuminator 50 such that the light emitting directions of the light emitting diodes 20 are substantially parallel to the optical axis 1A, and because the mirror groups 30 and the lens 54 are arranged downstream of the light emitting directions, the size of the ring illuminator 50 in the radial direction about the optical axis 1A can be reduced. Hence, when the ring illuminator 50 is mounted to the objective lens 1, the ring illuminator 50 does not interfere in obtaining a measurement and thus the measuring operation can be speedily performed.

In various exemplary embodiments of the second exemplary embodiment of the ring illuminator 40 shown in FIG.

4, by using the lens 54, which is a general-purpose optical element, it is possible to manufacture the ring illuminator 50 at a low cost. At the same time, because the lens 54 has high transmissivity and high accuracy, the transmission loss of the illumination light can be reduced to a small amount. Thus, it is possible to accurately focus the illumination light on an illumination range such that the illumination efficiency can be further enhanced.

In various exemplary embodiments of the second exemplary embodiment of the ring illuminator 40 shown in FIG. 4, the objective lens 1 can penetrate the ring illuminator 50 through the central hole 55 formed in the center portion of the lens 54. As a result, the reflection light from the object to be measured 3 reaches the objective lens 1 without being interrupted. Hence, the measurement of the object to be measured 3 can be surely performed.

Figure 5:
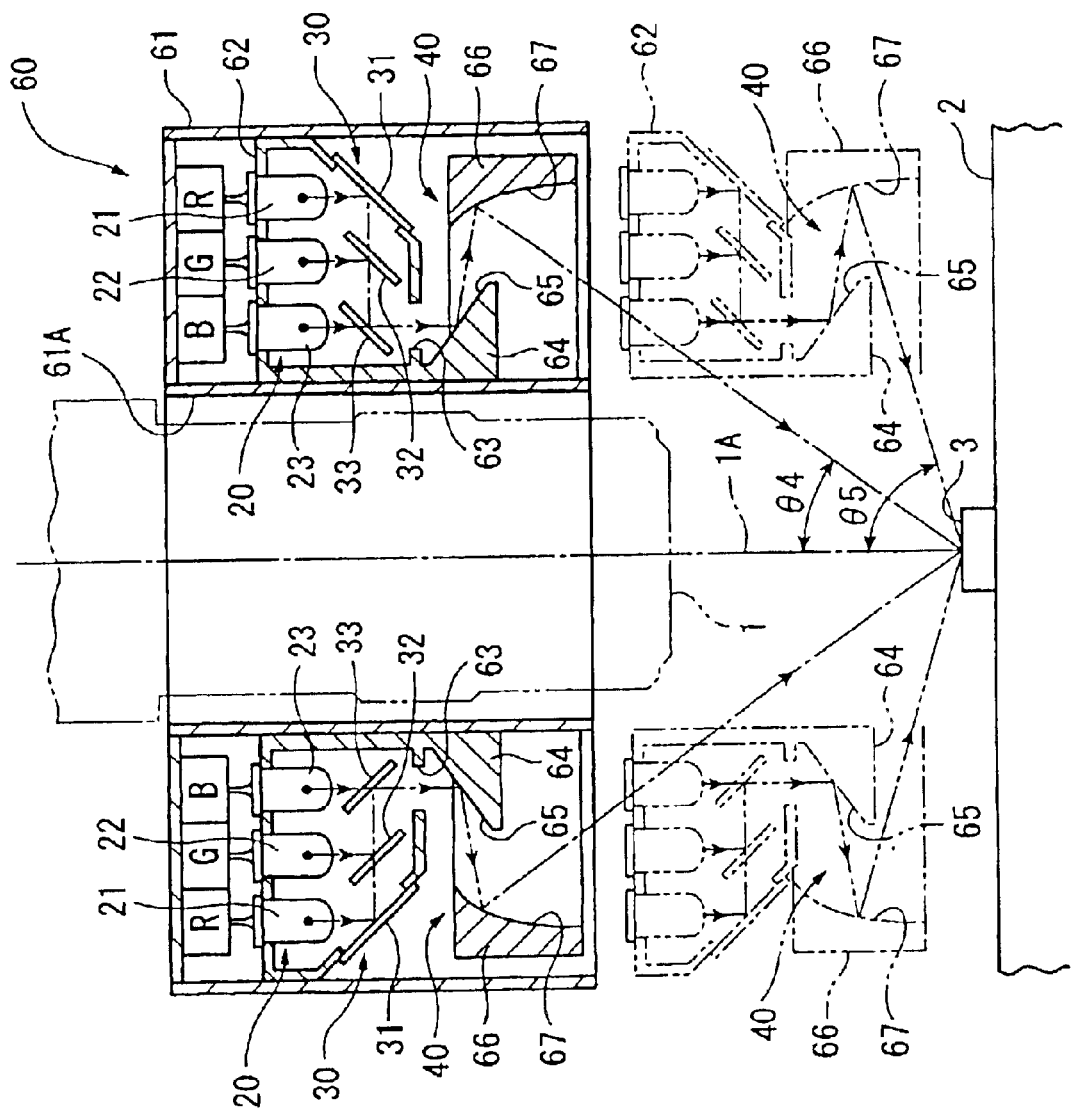
FIG. 5 is a cross-sectional view of a third exemplary embodiment of a ring illuminator according to this invention.

FIG. 5 is a cross-sectional view of a third exemplary embodiment of a ring illuminator 60 according to this invention. The ring illuminator 60 differs from the above-mentioned first embodiment of the ring illuminator 10 in the orientation of the light emitting diodes 20 as the light source and in the constitution of the reflection mirror 40, which acts as the focusing unit. In other respects, the ring illuminator 60 is substantially similar to the ring illuminator 10.

As shown in FIG. 5, the ring illuminator 60 includes a casing 61 and a light source box 62. The casing 61 is formed in a downwardly opened ring shape and is provided with a lens through hole 61 A which vertically penetrates a center portion of the casing 61. The light source box 62 is mounted to the casing 61.

The light source box 62 houses the light emitting diodes 20 and the mirror groups 30 and is provided with slits 63 in a bottom wall of the light source box 51 faces the object to be measured 3. The slits allow the combined illumination light to pass out of the light source box 62. In various exemplary embodiments, the slits 63 are formed in the bottom wall at a location that is close to the objective lens 1.

As shown in FIG. 5, the red, green and blue light emitting diodes 21, 22 and 23 are each arranged in a ring shape in a plane that is substantially orthogonal to the optical axis 1A. In various exemplary embodiments, each set of the light emitting diodes 21, 22 and 23 is arranged in an annular shape, where the annular shapes differ in distance from the optical axis 1A and the sets are spaced apart from each other at a given interval. In the exemplary embodiment shown in FIG. 5, from the side closest to the optical axis 1A, the light emitting diodes 23 of blue color (B), the light emitting diodes 22 of green color (G) and the light emitting diodes 21 of red color (R) are sequentially arranged. The light emitting directions of the light emitting diodes 20 are substantially parallel to the optical axis 1A, such that the light emitting directions extend toward the object to be measured 3.

Mirror groups 30, which are generally similar to the mirror groups 30 of the above-mentioned first embodiment of the ring illuminator 10, are arranged downstream of the light emitting directions of the light emitting diodes 20. Because of these mirror groups 30, the light beams radiated from the red, green and blue light emitting diodes 21, 22 and 23 are reflected by a mirror of the mirror group 30, or are allowed to pass through that mirror of the mirror group 30, in a direction away from the optical axis 1A. The mirrors group 30 of the ring illuminator 50 combine the light emitted by the light emitting diodes 20 in a manner similar to that of the mirror groups 30 of the ring illuminator 10 to form the combined illumination light of a given hue. The combined illumination light is directed by the mirror group 30 substantially parallel to the optical axis 1A and advances through the slits 63 of the light source box 62.

As shown in FIG. 5, the ring illuminator 60 also includes a reflection mirror 40, which forms at least a portion of the focusing unit. The reflection mirror 40 is positioned inside of the casing 61 at a side of the light source box 62 that faces the object to be measured 3.

The reflection mirror 40 includes a first reflection mirror 64 and a second reflection mirror 66. The first reflection mirror 64 includes a first reflection surface 65 formed in a planar shape. This first reflection surface 65 reflects the illumination light passing through the slits 63 in the direction away from the optical axis 1A. In various exemplary embodiments, the first reflection mirror 64 is integrally fixed to the light source box 62.

The second reflection mirror 66 includes a second reflection surface 67 formed in a curved shape having a convex curvature in the direction away from the optical axis 1A. In various exemplary embodiments, the convex curvature of the second reflection surface 67 is defined with respect to the cross-sectional direction along the optical axis 1A and the planar direction substantially orthogonal to the optical axis 1A, such that the illumination light reflected from the first reflection surface 65 onto the second reflection surface 67 is reflected towards and focused on the object to be measured 3 by the second reflection surface 67 at a position-dependent illumination angle. In various exemplary embodiments, the relative position of the second reflection mirror 66 with respect to the first reflection mirror 64 is movable along the optical axis 1A by a driving device (not shown in the drawing) mounted inside the casing 61, to alter the position-dependent illumination angle.

To adjust the position-dependent illumination angle, from a small illumination angle θ4 to a large illumination angle θ5, of the illumination light on the object to be measured 3 provided by the ring illuminator 60, the second reflection mirror 66 is moved relative to the first reflection mirror 64 toward the light source box 62 side along the optical axis 1A, as indicated by a chain double-dashed line shown in FIG. 5. At the same time, the mounting position of the ring illuminator 60 on the objective lens 1 is set at a position close to the object to be measured 3. Due to this relative movement, the combined illumination light reflected from the first reflection surface 65 is incident on the second reflection surface 67 of the second reflection mirror 66 at a position close to the object to be measured 3. That is, the combined illumination light is incident on the second reflection surface 67 at a position where an inclination angle with respect to the optical axis 1A is small. Accordingly, the reflected combined illumination light is directed to the object to be measured 3 at the large illumination angle θ5 with respect to the optical axis 1A.

In various exemplary embodiments of the third exemplary embodiment of the ring illuminator 60 shown in FIG. 5, the light beams that radiate from the red, green and blue light emitting diodes 21, 22 and 23 are combined to form a combined illumination light of a given hue by the mirror group 30 including the dichroic mirrors 32 and 33. The dichroic mirrors 32 and 33 are arranged in front of two of the light emitting diodes 21, 22 and 23. The combined illumination light is directed to the object to be measured 3. Hence, it is possible to illuminate the surface of the object to be measured 3 with illumination light having a hue corresponding to a surface color of the object to be measured 3. In response, the contrast within the image of the object to be measured 3 obtained through the objective lens 1 is emphasized. Hence, it is possible to sufficiently enhance the accuracy of detection of edges or the like of the object be measured 3 in the obtained image.

In various exemplary embodiments of the third exemplary embodiment of the ring illuminator 60 shown in FIG. 5, by combining the radiated light beams output from the red, green and blue light emitting diodes 21, 22 and 23 using the mirror groups 30, the combined illumination light that is preliminarily combined into the given hue by the mirror group 30 is directed to the object to be measured 3. Accordingly, compared to situations in which the light beams of respective colors are combined at the surface of the object to be measured 3, it is possible to radiate the combined illumination light having a uniform hue free from irregularities, so that the detection accuracy can be further enhanced.

In various exemplary embodiments of the third exemplary embodiment of the ring illuminator 60 shown in FIG. 5, by concentrating the illumination light on the object to be measured 3 by the reflection mirror 40, the illumination efficiency is enhanced. Consequently, the number of light emitting diodes 20 required in the ring illuminator 10 can be reduced. As a result, the size of the ring illuminator 10 can be reduced.

In various exemplary embodiments of the third exemplary embodiment of the ring illuminator 60 shown in FIG. 5, compared to the related art, the number of light emitting diodes 20 required in the ring illuminator 10 can be reduced. Hence, the adverse influence of heat generated from the light emitting diodes 20 on the image measuring device or the like can be reduced. At the same time, the power consumption and the power cost of the ring illuminator can be reduced.

In various exemplary embodiments of the third exemplary embodiment of the ring illuminator 60 shown in FIG. 5, by using the light emitting diodes 20 as the light source, it is possible to provide a light source having the more-rapid responsivity and the longer lifetime which are features of light emitting diodes. Further, by providing with the provision of the light emitting diodes 21, 22 and 23 of different colors, the white illumination light can be generated. At the same time, by properly changing the ratio of red, green and blue light on the combined illumination light, it is possible to generate illumination light beams having various hues. Accordingly, it is possible directed illumination light of an optimum hue or desired hue to the object to be measured 3 corresponding to the object to be measured 3 having various surface colors.

In various exemplary embodiments of the third exemplary embodiment of the ring illuminator 60 shown in FIG. 5, by using the dichroic mirrors 32 and 33 as part of the mirror group 30 that forms the combining unit, it is possible to output illumination light of the given hue. Further, by forming the dichroic mirrors 32 and 33 in a substantially rectangular planar simple shape, it is possible to form the mirror group 30 in an inexpensive manner. Still further, compared to a case in which dichroic mirrors having curved surfaces are used, the loci of the reflected and transmitted light beams can be easily determined. Hence, it is possible to arrange and mount the dichroic mirrors 32 and 33 easily. At the same time, it is possible to accurately combine the illumination light from the various groups of the red, green and blue light emitting diodes 21, 22 and 23.

In various exemplary embodiments of the third exemplary embodiment of the ring illuminator 60 shown in FIG. 5, the mirrors 32 and 33 are dichroic mirrors in which there is only a single transition from reflective to transmissive or from transmissive to reflective, corresponding to a given wavelength of the light. Accordingly, compared to dichroic mirrors that transition from reflective to transmissive or from transmissive to reflective at a plurality of different wavelengths of the light, the number of layers of mirror surface vapor deposited films of the dichroic mirrors 32 and 33 can be reduced. Hence, the film forming processing can be facilitated and, at the same time, the reflection transmission efficiencies of the dichroic mirrors 32 and 33 can be enhanced.

In various exemplary embodiments of the third exemplary embodiment of the ring illuminator 60 shown in FIG. 5, by forming the ring illuminator 60 such that the light emitting directions of the light emitting diodes 20 are substantially parallel to the optical axis 1A and because the mirror groups 30 and the first reflection mirror 64 and the second reflection mirror 66 are arranged downstream of the light emitting directions, the size of the ring illuminator 60 in the radial direction about the optical axis 1A can be reduced. Hence, when the ring illuminator 60 is mounted to the objective lens 1, the ring illuminator 60 does not interfere in obtaining a measurement, so that the measuring operation can be speedily performed.

In various exemplary embodiments of the third exemplary embodiment of the ring illuminator 60 shown in FIG. 5, the convex curvature is provided to the reflection surface 67 of the second reflection mirror 66 in the direction away from the optical axis 1A with respect to the cross-sectional direction along the optical axis 1A and the planar direction substantially orthogonal to the optical axis 1A. Hence, it is possible to direct the illumination light to the position to be measured of the object to be measured 3 in a concentrated manner such that the illumination efficiency can be further enhanced.

In various exemplary embodiments of the third exemplary embodiment of the ring illuminator 60 shown in FIG. 5, by enabling the second reflection mirror 66 to move relative to the first reflection mirror 64 in the direction along the optical axis 1A, the illumination light is reflected from the second reflection surface 67 of the second reflection mirror 66 at positions which have different inclination angles. Consequently, the reflection angle can be changed. As a result, the illumination angle of the combined illumination light or the object to be measured 3 can be adjusted. Accordingly, the illumination light having a desired illumination angle, which can be selected based on the size, the shape and/or the surface condition of the object to be measured 3, is obtained. Therefore, the accuracy of detection of edges or the like of the object to be measured 3 in the obtained image can be further enhanced.

This invention is not limited to the above-mentioned exemplary embodiments. For example, although the explanation has been made with respect to a ring illuminator that is used with the image measuring device in the above-mentioned respective exemplary embodiments, the ring illuminator according to this invention can be used with a measuring microscope, a tool microscope, a projector, a three-dimensional image measuring apparatus or the like.

Further, although the ring illuminator is mounted on the objective lens 1 in the above-mentioned respective embodiments, this invention is not limited to such a manner of mounting. That is, the ring illuminator according to this invention may be mounted on the body of the measuring device or the like or the measuring base console. Further, a member which supports the ring illuminator according to this invention can be provided apart from these measuring devices and the ring illuminator may be mounted on the member. Further, the mounting method is not limited to using three screws supported such that the screws are movable toward or away from the objective lens 1. Rather, any known or later-developed method that can appropriately set the operable distance between the ring illuminator and the object to be measured can be used. Further, the mounting method may use a structure which is movable along the optical axis of the optical system.

Further, the light emitting diodes 20 are arranged in a substantially rectangular shape in various ones of the above-mentioned respective exemplary embodiments. However, this invention is not limited to such an arrangement. Rather, the light emitting diodes 20 may be arranged in a substantially circular shape, in a substantially triangular shape, in a pentagonal shape, in a polygonal shape, or any other useful shape.

Further, the arrangement of the light emitting diodes 21, 22 and 23 of respective colors R, G and B is not limited to the sequences indicated in the above-mentioned respective exemplary embodiments. That is, a different arrangement may be adopted. In this case, it is possible to use dichroic mirrors having reflective or transmissive characteristics corresponding to the arrangement of the differently colored light emitting diodes 21, 22 and 23. Further, it is also possible to use dichroic mirrors which transition between reflective and transmissive characteristics at a plurality of wavelengths.

Further, in addition to, or in place of, the red, green and blue light emitting diodes 21, 22 and 23, a white light emitting diode may be used. When such a white light emitting diode is used, it is possible to adjust the hue of the illumination light without lowering the brightness.

Further, although the casing and the light source box are formed by processing the metal sheet material in the above-mentioned respective embodiments, the material is not limited to metal sheet material and may be made of synthetic resin or any other suitable material. Further, the reflection mirror is made of metal, where a mirror finish is provided on the reflection surface of the reflection mirror. However, the reflection mirror may be made of glass, synthetic resin or any other suitable material. Moreover, only the reflection surface may be made of glass, metal or any other suitable material. Furthermore, plating or the like may be applied to the reflection surface.

While this invention has been described in conjunction with the exemplary embodiments outlined above, various alternatives, modifications, variations, improvements, and/ or substantial equivalents, whether known or that are or may be presently unforeseen, may become apparent to those having at least ordinary skill in the art. Accordingly, the exemplary embodiments of the invention, as set forth above, are intended to be illustrative, not limiting. Various changes may be made without departing from the spirit and scope of the invention. Therefore, the claims as filed and as they may be amended are intended to embrace all known or later-developed alternatives, modifications variations, improvements, and/or substantial equivalents.

What is claimed is:

1. A ring illuminator, comprising:
a light source that includes a plurality of light emitting elements that are arranged around an optical axis of an optical system, the light emitting elements including at least two groups of light emitting elements having light emitting colors different from each other, each group of light emitting elements that emit the same color light being arranged in a substantially ring shaped configuration around the optical axis on a ring plane oriented substantially orthogonally to the optical axis;

a combining unit that combines light beams radiating from the light emitting elements and having light emitting colors different from each other to generate illumination light having a given hue, the combining unit located downstream from the light emitting elements along light emitting directions of the light emitting elements; and a focusing unit that focuses the illumination light at a given position along the optical axis, the focusing unit located downstream from the combining unit along an advancing direction of the generated illumination light from the combining unit, the advancing direction extending substantially parallel to the ring plane, the focusing unit including a reflection mirror that reflects and focuses the illumination light from the combining unit to the given position.

2. A ring illuminator according to claim 1, wherein:
the light emitting element groups, having different light emitting colors and arranged in a ring shape, are arranged in a spaced apart manner from each other at a given distance along the optical axis direction; and
the light emitting directions of the light emitting element groups extend in a direction away from the optical axis.

3. A ring illuminator according to claim 1, wherein:
the light emitting element groups, having different light emitting colors and arranged in the substantially ring shaped configuration, are arranged in a spaced apart manner for each other at different base distances from the optical axis, and
the light emitting direction extends in the direction substantially parallel to the optical axis.

4. A ring illuminator according to claim 1, wherein the plurality of light emitting elements comprise three groups of light emitting diodes having respective light emitting colors of red (R), green (G) and blue (B).

5. A ring illuminator according to claim 1, wherein the combining unit includes at least one dichroic mirror formed in a planar shape.

6. A ring illuminator according to claim 5, wherein, for each dichroic mirror, that dichroic mirror reflects light having a wavelength shorter than a given wavelength and allows light having a wavelength longer than the given wavelength to pass through that dichroic mirror or allows light having a wavelength shorter than a given wavelength to pass through and reflects light having a wavelength longer than the given wavelength.

7. A ring illuminator according to claim 1, wherein:
the advancing direction of the illumination light generated by the combining unit extends substantially orthogonal to the optical axis and away from the optical axis;
the focusing unit includes a reflection mirror that focuses the illumination light in the optical axis direction; and
the reflection mirror includes a reflection surface having respective given curvatures with respect to two cross-sectional directions parallel to and orthogonal to the optical axis.

8. A ring illuminator, comprising:
a light source that includes a plurality of light emitting elements that are arranged around an optical axis of an optical system, the light emitting elements including at least two groups of light emitting elements having light emitting colors different from each other, each group of light emitting elements that emit the same color light being arranged in a substantially ring shaped configuration around the optical axis on a ring plane oriented substantially orthogonally to the optical axis;

a combining unit that combines light beams radiating from the light emitting elements and having light emitting colors different from each other to generate illumination light having a given hue, the combining unit located downstream from the light emitting elements along light emitting directions of the light emitting elements; and a focusing unit that focuses the illumination light at a given position along the optical axis, the focusing unit located downstream from the combining unit along an advancing direction of the generated illumination light from the combining unit, wherein:

the advancing direction of the illumination light generated by the combining unit extends substantially parallel to the optical axis;

the focusing unit includes:
 a first reflection mirror that reflects the illumination light in a direction away from the optical axis, and
 a second reflection mirror that focuses the illumination light reflected from the first reflection mirror and directs the illumination light along the optical axis direction; and at least one of the first reflection mirror and the second reflection mirror includes a reflection surface having respective given curvatures with respect to two cross-sectional directions parallel to and orthogonal to the optical axis.

9. A ring illuminator according to claim 1, wherein:

the light source and the combining unit are fixed to an illuminator body;

the focusing unit is mounted such that the focusing unit is relatively movable with respect to the illuminator body in a direction substantially parallel to the optical axis; and the ring illuminator includes an adjusting unit that adjusts a position where the illumination light is focused by relatively moving the illuminator body and the focusing unit.

10. A ring illuminator, comprising:

a light source that includes a plurality of light emitting elements that are arranged around an optical axis of an optical system, the light emitting elements including at least two groups of light emitting elements having light emitting colors different from each other, each group of light emitting elements that emit the same color light being arranged in a substantially ring shaped configuration around the optical axis on a ring plane oriented substantially orthogonally to the optical axis;

a combining unit that combines light beams radiating from the light emitting elements and having light emitting colors different from each other to generate illumination light having a given hue, the combining unit located downstream from the light emitting elements along light emitting directions of the light emitting elements; and a focusing unit that focuses the illumination light at a given position along the optical axis, the focusing unit located downstream from the combining unit along an advancing direction of the generated illumination light from the combining unit, wherein:

the advancing direction of the illumination light generated by the combining unit extends substantially parallel to the optical axis; and the focusing unit includes a substantially torus-shaped lens having a hole at a center portion of the lens.

11. A ring illuminator according to claim 8, wherein:

the light emitting element groups, having different light emitting colors and arranged in the substantially ring shaped configuration, are arranged in a spaced apart manner from each other at a given distance along the optical axis direction; and the light emitting directions of the light emitting element groups extend in a direction away from the optical axis.

12. A ring illuminator according to claim 8, wherein:

the light emitting element groups, having different light emitting colors and arranged in a ring shape, are arranged in a spaced apart manner for each other at different base distances from the optical axis, and the light emitting direction extends in the direction substantially parallel to the optical axis.

13. A ring illuminator according to claim 8, wherein the combining unit includes at least one dichroic mirror formed in a planar shape.

14. A ring illuminator according to claim 8, wherein:

the advancing direction of the illumination light generated by the combining unit extends substantially orthogonal to the optical axis and away from the optical axis;

the focusing unit includes a reflection mirror that focuses the illumination light in the optical axis direction; and the reflection mirror includes a reflection surface having respective given curvatures with respect to two cross-sectional directions parallel to and orthogonal to the optical axis.

15. A ring illuminator according to claim 8, wherein:

the light source and the combining unit are fixed to an illuminator body;

the focusing unit is mounted such that the focusing unit is relatively movable with respect to the illuminator body in a direction substantially parallel to the optical axis; and the ring illuminator includes an adjusting unit that adjusts a position where the illumination light is focused by relatively moving the illuminator body and the focusing unit.

16. A ring illuminator according to claim 10, wherein:

the light emitting element groups, having different light emitting colors and arranged in the substantially ring shaped configuration, are arranged in a spaced apart manner from each other at a given distance along the optical axis direction; and the light emitting directions of the light emitting element groups extend in a direction away from the optical axis.

17. A ring illuminator according to claim 10, wherein:

the light emitting element groups, having different light emitting colors and arranged in a ring shape, are arranged in a spaced apart manner for each other at different base distances from the optical axis, and the light emitting direction extends in the direction substantially parallel to the optical axis.

18. A ring illuminator according to claim 10, wherein the combining unit includes at least one dichroic mirror formed in a planar shape.

19. A ring illuminator according to claim 10, wherein:

the advancing direction of the illumination light generated by the combining unit extends substantially orthogonal to the optical axis and away from the optical axis;

the focusing unit includes a reflection mirror that focuses the illumination light in the optical axis direction; and the reflection mirror includes a reflection surface having respective given curvatures with respect to two cross-sectional directions parallel to and orthogonal to the optical axis.

20. A ring illuminator according to claim 10, wherein:

the light source and the combining unit are fixed to an illuminator body;

the focusing unit is mounted such that the focusing unit is relatively movable with respect to the illuminator body in a direction substantially parallel to the optical axis; and the ring illuminator includes an adjusting unit that adjusts a position where the illumination light is focused by relatively moving the illuminator body and the focusing unit.

* * * * *